United States Patent [19]

Volk

[11] Patent Number: 4,721,378

[45] Date of Patent: Jan. 26, 1988

[54] CONDENSING-IMAGE FORMING OPTICAL SYSTEM FOR INDIRECT OPHTHALMOSCOPY

[76] Inventor: David Volk, 3336 Kersdale Rd., Pepper Pike, Ohio 44124

[21] Appl. No.: 779,799

[22] Filed: Sep. 24, 1985

[51] Int. Cl.$^4$ .................. A61B 3/12; G02B 13/18
[52] U.S. Cl. ..................... 351/205; 350/432
[58] Field of Search ............... 351/205, 221; 350/96.32, 432

[56] References Cited

U.S. PATENT DOCUMENTS

| | | | |
|---|---|---|---|
| 3,881,812 | 5/1975 | Ben-Tovim | 351/205 |
| 4,015,898 | 4/1977 | Schirmer | 351/205 X |
| 4,583,539 | 4/1986 | Karlin et al. | 350/96.32 |

*Primary Examiner*—Rodney B. Bovernick
*Attorney, Agent, or Firm*—Baldwin, Egan, Hudak & Fetzer

[57] ABSTRACT

This invention pertains to a novel compact hand-held optical system whch is used both as a light condenser and as an aerial image former in the examination of the fundus of the eye with the indirect ophthalmoscope and with the slit lamp biomicroscope.

The novel optical system has the unique feature that the aerial image of the fundus produced by it is upright rather than inverted as in the present state of the art with hand-held indirect ophthalmoscopy lenses. The novel optical system consists of three coaxial air-spaced double aspheric lenses which are so designed and positioned as to converge the illuminating light beam from the light source such that an image of said source is formed at the center of the pupil of the examined eye, the light then diverging from said image to illuminate the fundus of the eye. The light emerging from the eye through its pupil is then refracted by the novel optical system to form an upright aerial image of the fundus between the lens system and the indirect ophthalmoscope with which the upright aerial image is viewed, in a first embodiment of the invention, and between the lens system and the slit lamp biomicroscope with which the upright aerial image is viewed, in a second embodiment of the invention.

5 Claims, 5 Drawing Figures

CONDENSING-IMAGE FORMING OPTICAL SYSTEM FOR INDIRECT OPHTHALMOSCOPY

Indirect ophthalmoscopy may be defined as the examination of the fundus of the eye by the observation of a real aerial image of the fundus. Said observation is usually performed with a binocular indirect ophthalmoscope, but is increasingly being done with the binocular slit lamp biomicroscope.

This invention pertains to a novel compact hand-held optical system which is used both as a light condenser and an aerial image former in the examination of the aerial image of the fundus of the eye with the indirect ophthalmoscope and with the slit lamp biomicroscope.

The optical system has the unique feature that the aerial image of the fundus produced by it is upright rather than inverted as is the case with prior art indirect ophthalmoscopy lenses which form an inverted aerial image of the fundus which is then viewed with the indirect ophthalmoscope and with the slit lamp biomicroscope.

The examiner viewing the inverted aerial image must mentally reorient what he sees to correspond to the actual position of parts of the fundus. This can be confusing to an ophthalmologist who may be treating a retinal lesion such as a retinal tear or a retinal tumor. The image seen is diametrically opposed to the actual position of parts of the fundus.

The novel optical system of this invention, consisting of a minimum of three coaxial properly spaced double aspheric lenses, inverts the aerial image so that it is seen in its correct relationship to the fundus.

BACKGROUND OF THE INVENTION

The first hand-held indirect ophthalmoscopy lens which was used as a condensing and image-forming lens, was spherical and of low power, +13.00 diopters. The aerial image produced with this spherical lens was magnified, inverted, and quite blurred towards the periphery. In 1958, Sudarsky and Volk in their paper entitled "Aspherical Objective Lens As an Aid in Indirect Ophthalmoscopy", *American Journal of Ophthalmology*, Vol. 46, No. 4, April 1959, described their preliminary results using aspheric condensing-image forming lenses for indirect ophthalmoscopy.

In my copending U.S. patent application, "Lens for Indirect Ophthalmoscopy", Ser. No. 437,279, filed Oct. 28, 1982, the lens is designed with two different conoid surfaces, with the aerial image of the fundus almost entirely aberration-free. In my copending patent application "Indirect Ophthalmoscopy Lens for Use with Slit Lamp Biomicroscope", Ser. No. 727,764, now U.S. Pat. No. 4,627,694 filed May 1, 1985, the indirect ophthalmoscopy lens for use with the slit lamp biomicroscope is a symmetrical double aspheric very high powered lens, with nominal dioptric powers ranging from 60 diopters to 130 diopters. With all of the prior art indirect ophthalmoscopy lens, the aerial image produced is inverted. The novel optical system of this invention produces an upright clear aerial image of the fundus which is viewed with the indirect ophthalmoscope and with the slit lamp biomicroscope.

DESCRIPTION OF THE DRAWINGS

FIG. 2, drawn to scale, of a first embodiment of the novel optical system of this invention, primarily intended for use with the indirect ophthalmoscope, illustrates schematically the light condensing function of the novel optical system. This system is illustrated schematically in FIG. 1 as being supported or held in lens housing L. Aspheric lenses A, B, and C are coaxial and together represent the fundamental optical arrangement of the novel optical system of this invention. The light rays from the indirect ophthalmoscope incident upon lens A are converged to focus $f_{A\,back}$ of lens A which focus is also $f_{B\,front}$ of lens B. Light rays from $f_{B\,front}$ are refracted through lens B to a parallel bundle of light rays which are incident upon lens C. Lens C converges said light rays toward its back focus, $f_{C\,back}$ at the center of the entrance pupil of the eye, and after refraction by the cornea of the examined eye, an image of the ophthalmoscope light source is formed at the center of the pupil of the eye. The light rays then diverge to illuminate the fundus. An axially concentric aperture stop, EE, is located in the combined posterior focal plane and anterior focal plane of lenses A and B respectively, and located as shown therebetween.

As an example of said first embodiment of the novel optical system of this invention, the focal distances of symmetrical coaxial lenses B and C when identical are 9.69 mm, so that lenses B and C are separated by a distance of 19.38 mm. Lens A coaxial with lenses B and C is a non-symmetrical double aspheric indirect ophthalmoscopy lens as described in my copending patent application, "Lens for Indirect Ophthalmoscopy", U.S. Ser. No. 437,279, of much lower power than lenses B and C, and of much larger diameter, approximately twice that of B and C. Lenses A and B are separated by a distance equal to the sum of the front focal distance, $f_{B\,front}$, of lens B, and the back focal distance, $f_{A\,back}$, of lens A. If the focal distance of lens B is 9.69 mm and the back focal distance of lens A is 21.27 mm, then A and B are separated by 30.96 mm. If the thickness of lens C is 7.66 mm and that of lens B is also 7.66 mm and that of lens A is 13.97 mm, then the length of the optical system is 79.63 mm.

Figure 1:
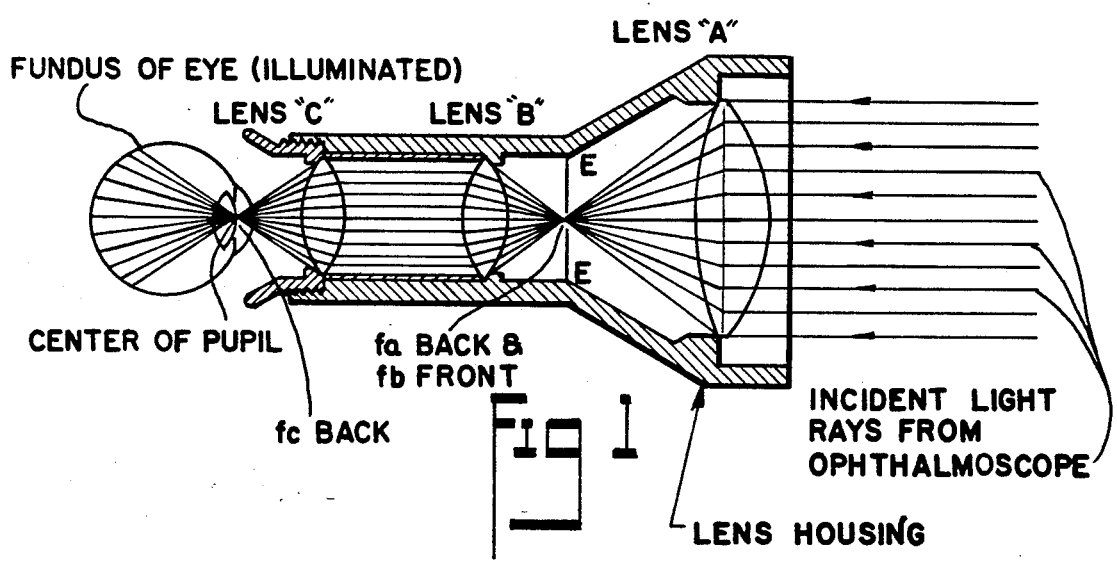
FIG. 1, drawn to scale, is a first embodiment of the novel optical lens system of this invention as being held in a lens housing.
Figure 2:
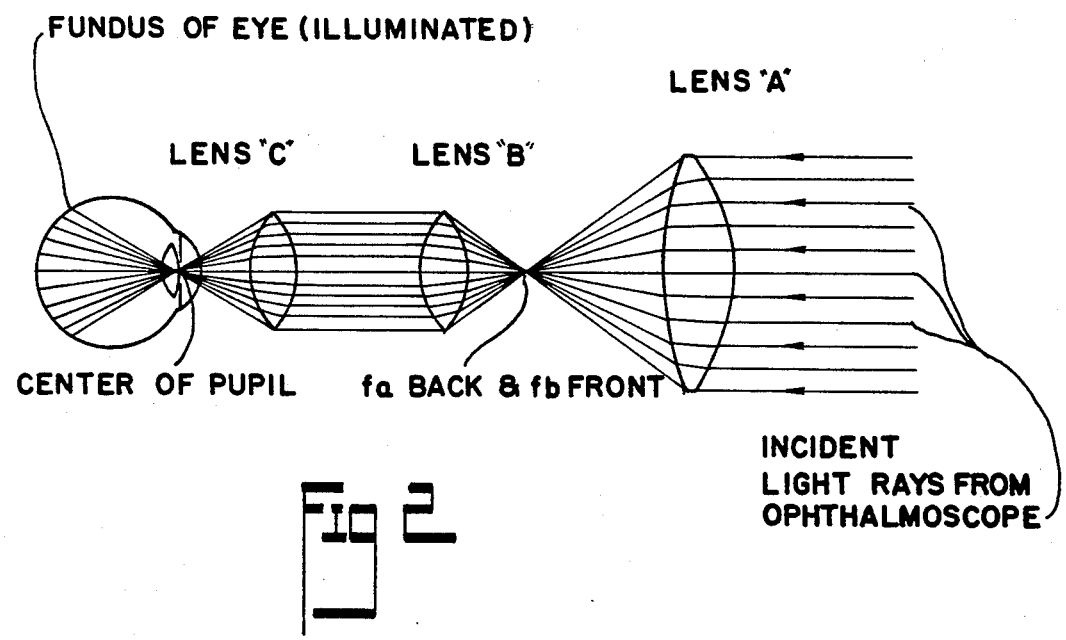
FIG. 2, drawn to scale, illustrates the light condensing function in a first embodiment of the novel optical system of this invention.
Figure 3:
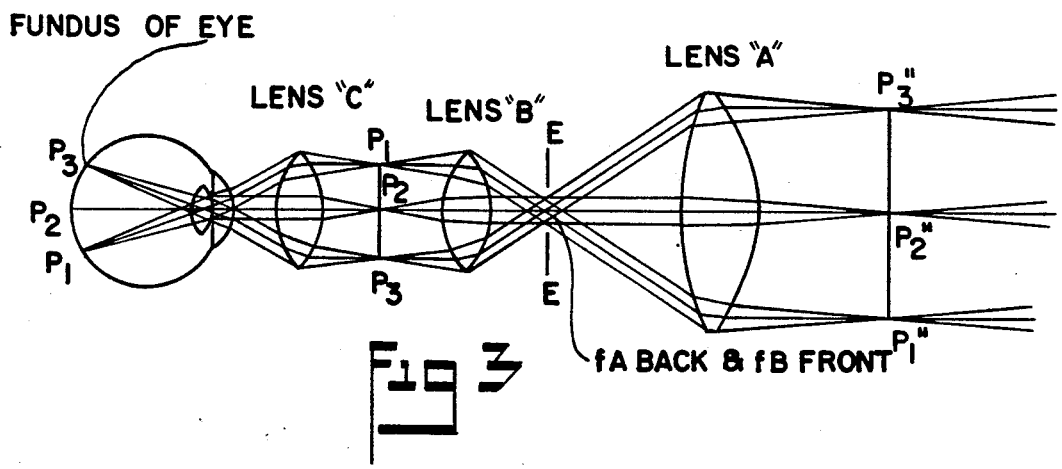
FIG. 3, drawn to scale, illustrates how the novel optical system of this invention in a first embodiment forms an upright magnified aerial image of the fundus.

In FIG. 3, drawn to scale, I have shown schematically how the novel optical system in said first embodiment of this invention forms an upright aerial image of the fundus in the anterior focal plane E—E of lens A. Homocentric bundles of diverging light rays from points in the illuminated fundus passing through the pupil and emerging from the cornea as homocentric bundles of parallel light rays are then incident upon the back surface of lens C; for example, light rays from points $P_1$, $P_2$, $P_3$. After refraction by lens C, an inverted image of the fundus is formed in the anterior focal plane of lens C. Note the reversal in position in said aerial image of points $P_1$, $P_2$, and $P_3$ in the fundus to $P_1'$, $P_2'$, and $P_3'$ in the anterior focal plane of lens C. Said image is then the object for lens B, and after refraction of light rays from said image by lens B, the light rays proceed as homocentric bundles of parallel light rays with the chief ray of all bundles passing through the anterior focus $f_B$ front of lens B which is also the back focus $f_{A\ back}$ of lens A, and proceeding to the back surface of lens A. After refraction by lens A, a reinverted upright magnified aerial image $P_1''$, $P_2''$, and $P_3''$ is formed in the anterior focal plane of lens A which image is viewed by means of an indirect ophthalmoscope. As in FIG. 1, aperture stop, EE, is located in the combined anterior focal plane of lens B and the posterior focal plane of lens A. The diameter of the aperture is approximately that of the dilated pupil of the eye, about 6 mm to 7 mm, allowing sufficient light to pass through for bright aerial image formation, while at the same time removing most of the stray light in the optical system.

Thus, by means of lenses B and C of the novel hand-held optical system, the position of points in the aerial image of the fundus formed by lens A $P_1''$, $P_2''$, $P_3''$ correspond to the actual position of points in the fundus itself.

Figure 4:
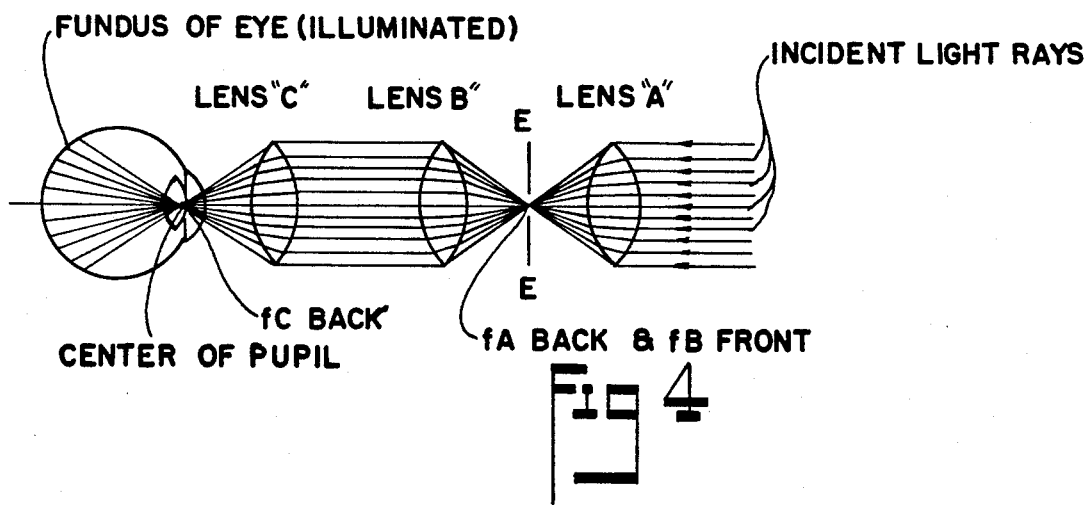
FIG. 4, drawn to scale, illustrates the light condensing function in a second embodiment of the novel optical system of this invention.

FIG. 4, drawn to scale, is a second embodiment of the novel optical system of this invention, primarily intended for use with the slit lamp biomicroscope, and illustrates schematically the light condensing function of the novel optical system. Aspheric lenses A, B, and C are coaxial, and as in the first embodiment, together represent the fundamental optical arrangement of the novel optical system of this invention. In this embodiment, lenses A, B, and C are all very strong biconvex symmetrical double aspheric lenses, each lens separated from its adjacent lens by a distance equal to the sum of the respective focal distances as measured from the apices of the opposing lens surfaces of said adjacent lenses. Generally, lenses A, B, and C are identical but may be moderately different in power as, for example, lens B being stronger in refractive power than lens C, and lens A being stronger in refractive power than, or equal to the refractive power of, lens B.

As an example of the second embodiment of the novel optical system of this invention, lenses A, B, and C are identical double aspheric symmetrical lenses with focal distances 9.69 mm and lens thickness of 7.66 mm. Lenses C and B are separated by a distance of 19.38 mm and lenses B and A are separated by the same distance. Taking into account the thicknesses of the three lenses, the length of this second embodiment of the novel optical system is 61.74 mm. Aperture stop, EE, is again located at the combined posterior focal plane and anterial focal plane of lenses A and B respectively.

Referring again to FIG. 4, I have shown schematically how the novel optical system of the second embodiment of this invention acts as a light condenser to converge the light beam from the slit lamp biomicroscope toward an image of the light source filament at the center of the entrance pupil of the eye, to be refracted by the cornea and aqueous humor to the center of the real pupil to then illuminate the fundus.

The light rays of the beam incident upon lens A are converged to focus $f_{A\ back}$ of lens A which is also $f_{B\ front}$ of lens B. Light rays from $f_{B\ front}$ are refracted through lens B to a parallel bundle of light rays which are incident upon lens C. Lens C converges said light rays towards its back focus, $f_{C\ back}$ at the center of the entrance pupil of the eye, and after refraction by the cornea of the examined eye, an image of the slit lamp biomicroscope light source is formed in the center of the pupil of the eye. The light rays then diverge to illuminate the fundus.

Figure 5:
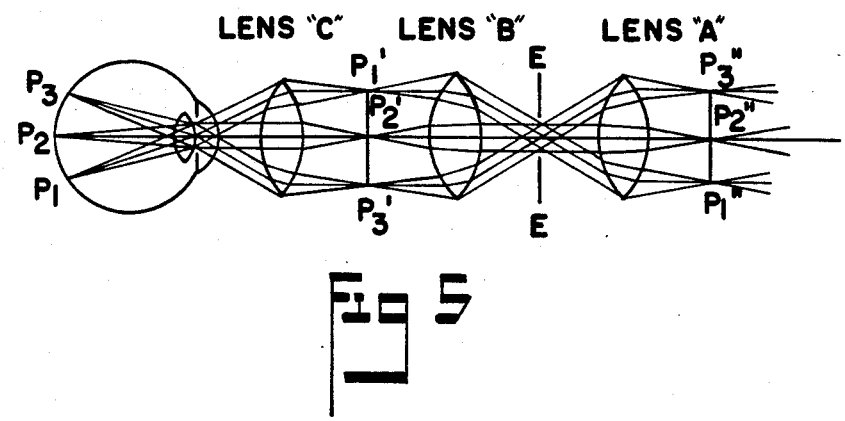
FIG. 5, drawn to scale, illustrates how the novel optical system of this invention in a second embodiment forms an upright aerial image of the fundus.

In FIG. 5, drawn to scale, I have shown schematically how the novel optical system in said second embodiment of this invention forms an upright aerial image of the fundus in the anterior focal plane of lens A. Homocentric bundles of diverging light rays from points in the fundus, passing through the pupil and emerging from the cornea as homocentric bundles of parallel light rays are then incident upon the back surface of lens C; for example, light rays from points $P_1$, $P_2$, $P_3$. After refraction by lens C, an inverted image of the fundus is formed in the anterior focal plane of lens C. Note the reversal in position in said aerial image of points $P_1$, $P_2$, and $P_3$ in the fundus to $P_1'$, $P_2'$, and $P_3'$ in the anterior focal plane of lens C. Said image is then the object for lens B, and after refraction of light rays from said image by lens B, the light rays proceed as homocentric bundles of parallel light rays with the chief ray of all bundles passing through the anterior focus $f_{B\ front}$ of lens B which is also the back focus $f_{A\ back}$ of lens A, and proceeding to the back surface of lens A. After refraction by lens A, a reinverted upright non-magnified aerial image $P_1''$, $P_2''$, and $P_3''$ is formed in the anterior focal plane of lens A, which image is viewed by means of a slit lamp biomicroscope. As stated earlier, aperture stop, EE, allows sufficient light to pass through for bright and clear aerial image formation.

Thus, by means of lenses B and C of the novel hand-held optical system, the position of points in the aerial image of the fundus formed by lens A, correspond to the actual position of points in the fundus itself.

FIGS. 1 through 5 and the description of said figures in the specification illustrate the differences in the two embodiments of this invention. In the first embodiment, for use with the indirect ophthalmoscope, the power of lens A is relatively low, resulting in a magnified aerial image of the fundus, which is desirable when the indirect ophthalmoscope, with its limited magnification, is used to view the aerial image of the fundus. In the second embodiment, for use with the slit lamp biomicroscope, the power of lens A is relatively high, being equal to or stronger than lenses B and C, resulting in a non-magnified or minified aerial image of the fundus. However, the slit lamp biomicroscope is itself capable of high magnification of the aerial image of the fundus, as much as 40 times with one type of slit lamp biomicroscope. It is, therefore, preferable, when using the slit lamp biomicroscope, to increase the power of lens A, thereby reducing the length of the optical system so that it may be conveniently used with said slit lamp biomicroscope.

All lenses in the novel optical system are mounted coaxially in an aluminum or plastic housing L at the properly spaced positions as shown in FIGS. 1 through 5. Each lens is multicoated to reduce surface reflections and to increase light transmission. To remove ultraviolet, violet, and blue light for protection and comfort of the patient, at least one of the three lenses may be made of yellow filter glass which absorbs almost all of the ultraviolet, violet, and blue light.

The use of double aspheric lenses in the novel optical system is essential if aberration-free aerial imagery is to be attained. Since the aerial image is formed chiefly of light in the red-orange portion of the visible spectrum, chromatic aberration is not significant.

Lenses A, B, and C are made of ophthalmic crown glass; however, they may be made of ophthalmic plastic, although plastic is easily scratched.

The novel optical system of this invention is designed to be hand-held but it may be advantageous to mount the novel optical system of the second embodiment in an adjustable mounting with respect to the patient's eye, for greater stability of said system.

I claim:

1. A compact condensing-image forming and image inverting optical system for indirect ophthalmoscopy for providing an upright aerial image of the fundus of the examined eye comprising a coaxial system of three bixconvex high powered double aspheric lenese of glass or plastic identified as lenses A, B and C fixed in predetermined spaced relation to each other along a longitudinal axis and with each lens being disposed with its major axis substantially perpendicular to a source of light rays, lens A being disposed to initially receive light rays from said source of light rays and to project said rays onto its adjacent lens B, lenses A and B being spaced from each other by a distance equal to the sum of the front focal distance $f_{B\,front}$ of lens B and the back focal distance $f_{A\,back}$ of lens A, lenses B and C being spaced apart at a distance equal to the sum of the front focal distance $f_{C\,front}$ of lens C and the back focal distance $f_{B\,back}$ of lens B, the said light rays incident upon lens A converging therefrom to the back focus $f_{A\,back}$ of lens A which focus is also the front focus $f_{B\,front}$ of lens B, said light rays from $f_{B\,front}$ of lens B being refracted through lens B to a parallel bundle of light rayes which are incident upon lens C, said lens C converging said light rays toward its back focus $f_{C\,back}$ at the center of the entrance pupil of the eye, and after refraction by the cornea of the examined eye an image of said light source is formed at the center of the pupil of the eye and said light rays then diverge to illuminate the fundus, homocentric bundles of diverging light rays from points in the illuminated fundus passing through the pupil and emerging from the cornea as homocentric bundles of parallel light rays which are then incident upon the adjacent surface of lens C and refracted by said lens C whereby an inverted image of the fundus is formed in the anterior focal plane of lens C, said inverted image is then the object of lens B, and light rays from said inverted image being then refracted by lens B whereby said light rays then proceed as homocentric bundles of parallel light rays with the chief ray of all bundles passing through the anterior focus $f_{B\,front}$ of lens B and proceed to lens A, and after refraction by said lens A, a reinverted upright aerial image is formed in the anterior focal plane of said lens A which image may then be viewed by means of an indirect ophthalmoscope.

2. A compact condensing-image forming and image inverting optical system for indirect ophthalmoscopy as in claim 1 wherein the three lenses are each symmetrical and are substantially of the same dioptric power and of the same diameter.

3. A compact condensing-image forming and image inverting optical system for indirect ophthalmoscopy as in claim 1 wherein the first of said lenses is of lower dioptric power and of larger diameter than the second and third lenses.

4. A compact condensing-image forming and image inverting optical system for indirect ophthalmoscopy as in claim 1 wherein at least one of the three lenses is made of yellow filter glass which transmits light fully in the green, yellow, orange, and red portion of the visible spectrum and is essentially opaque to blue, violet and ultraviolet light.

5. A compact condensing-image forming and image inverting optical system as defined in claim 1 and wherein said lenses are disposed and retained in their respective relative optical positions in said system within a housing.

* * * * *